US00PP19383P3

(12) United States Plant Patent
Goffreda et al.

(10) Patent No.: US PP19,383 P3
(45) Date of Patent: Oct. 28, 2008

(54) PEACH TREE NAMED 'NJF17'

(50) Latin Name: *Prunus persica*
Varietal Denomination: NJF17

(75) Inventors: Joseph C. Goffreda, Manapalan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 243 days.

(21) Appl. No.: 11/371,385

(22) Filed: Mar. 9, 2006

(65) Prior Publication Data

US 2007/0214524 P1 Sep. 13, 2007

(51) Int. Cl.
*A01H 5/00* (2006.01)

(52) U.S. Cl. ..... Plt./197

(58) Field of Classification Search ..... Plt./197
See application file for complete search history.

*Primary Examiner*—Kent L. Bell
*Assistant Examiner*—Georgia Helmer
(74) *Attorney, Agent, or Firm*—James A. Lucas; Driggs, Hogg, Daugherty & Del Zoppo, Co., L.P.A.

(57) ABSTRACT

A new and distinct peach variety of *Prunus persica* named 'NJF17' is described. This variety is distinguished from other peach varieties by its unique combination of non-showy, light pink flowers, flat fruit that ripen in early mid-season, bright green-yellow to yellow fruit that are devoid of over color, clingstone fruit with a juicy, nonmelting texture and sweet, spicy flavor, and firm fruit that retain their firmness well.

6 Drawing Sheets

Latin name of genus and species of the plant claimed: *Prunus persica* L.
Cultivar name: NJF17.

BACKGROUND OF THE INVENTION

The present invention relates to a new and distinct variety of peach tree named 'NJF17'. Our new tree resulted from crossing 'A43-143-782081' (unpatented) as the seed parent with 'D33-1-86227' (unpatented) peach tree, as the pollen parent. The new variety differs from seed parent 'A43-143-782081' in that the new variety has flat fruit while the seed parent has round fruit. The new variety differs from pollen parent 'D33-1-86277' in that the new variety has a sweet, spicy flavor while the pollen parent has a mild flavor. The resulting tree was selected when growing in a cultivated area as the 120$^{th}$ tree in the 91$^{st}$ row of Block D at the Rutgers Fruit Research and Extension Center in Cream Ridge, N.J.

BRIEF SUMMARY OF THE INVENTION

The 'NJF17' variety is distinguished from other peach varieties due to the following unique combination of characteristics:

Flat fruit shape.

Fruit devoid of over color.

Fruit with a bright green-yellow to yellow ground color.

Fruit with a sweet, spicy flavor.

Nonmelting flesh texture.

Firm fruit that retain their firmness well.

The variety was asexually reproduced at the Rutgers Fruit Research and Extension Center in Cream Ridge, N.J. Asexual reproduction of this new variety by budding onto >Lovell>rootstock shows that the foregoing characteristics are so reproduced.

The following detailed description concerns the original tree, 'NJF17'. The original tree and asexual progeny have been observed growing in a cultivated area at the Rutgers Fruit Research and Extension Center in Cream Ridge, N.J. Certain characteristics of this variety, such as growth and color, may change with changing environmental conditions (such as, light, temperature, moisture, nutrient availability, or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the peach tree by the best possible color representation using color photography. All color references below are measured against The Royal Horticultural Society (R.H.S.) Colour Chart. Colors are approximate as color depends on horticultural practices, such as light level, fertilization rate, and other conditions and, therefore, the color characteristics of this new variety should be determined with reference to the observations described herein, rather than from these illustrations alone. The following photographs were taken of a typical tree that was seven (7) years of age.

DETAILED BOTANICAL DESCRIPTION

Figure 1:
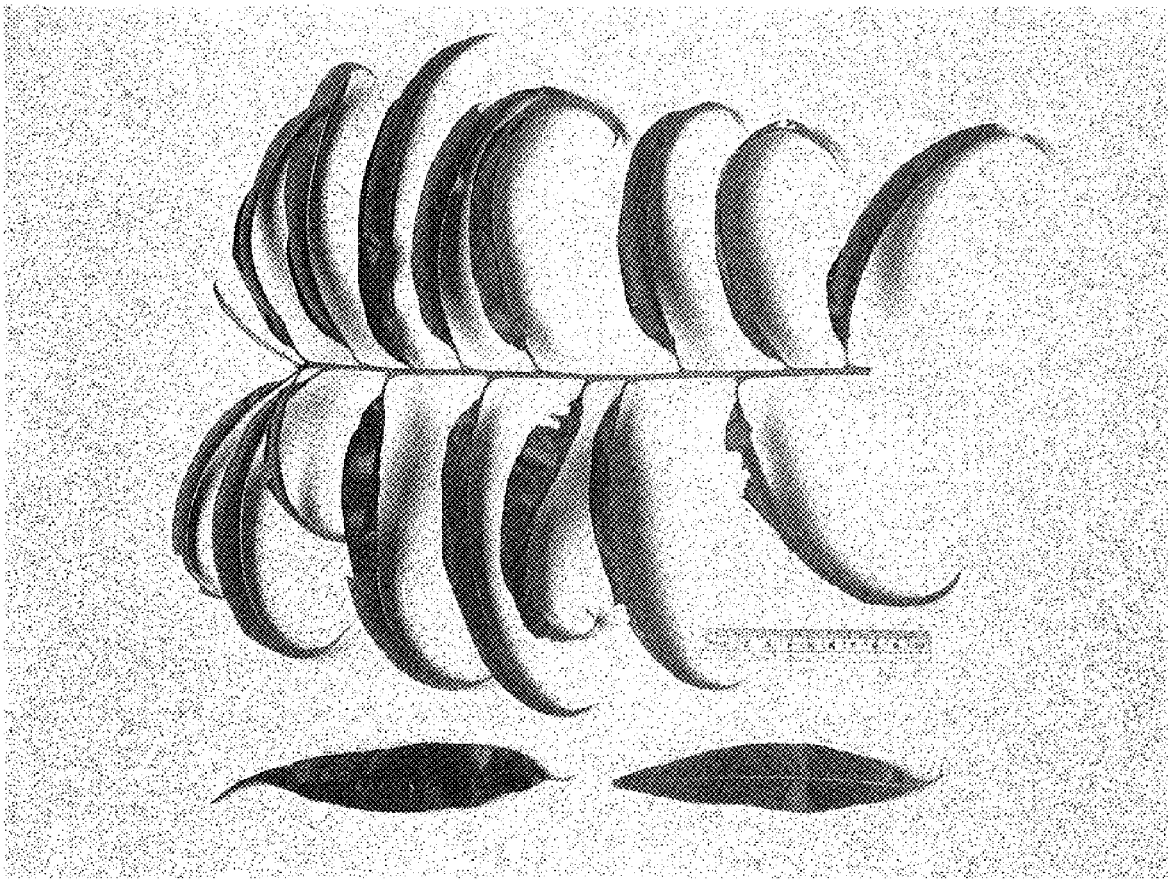
FIG. 1 is a color photograph taken on Aug. 19, 2005 of a characteristic twig of 'NJF17' in late summer bearing typical leaves of the mature foliage.
Figure 2:
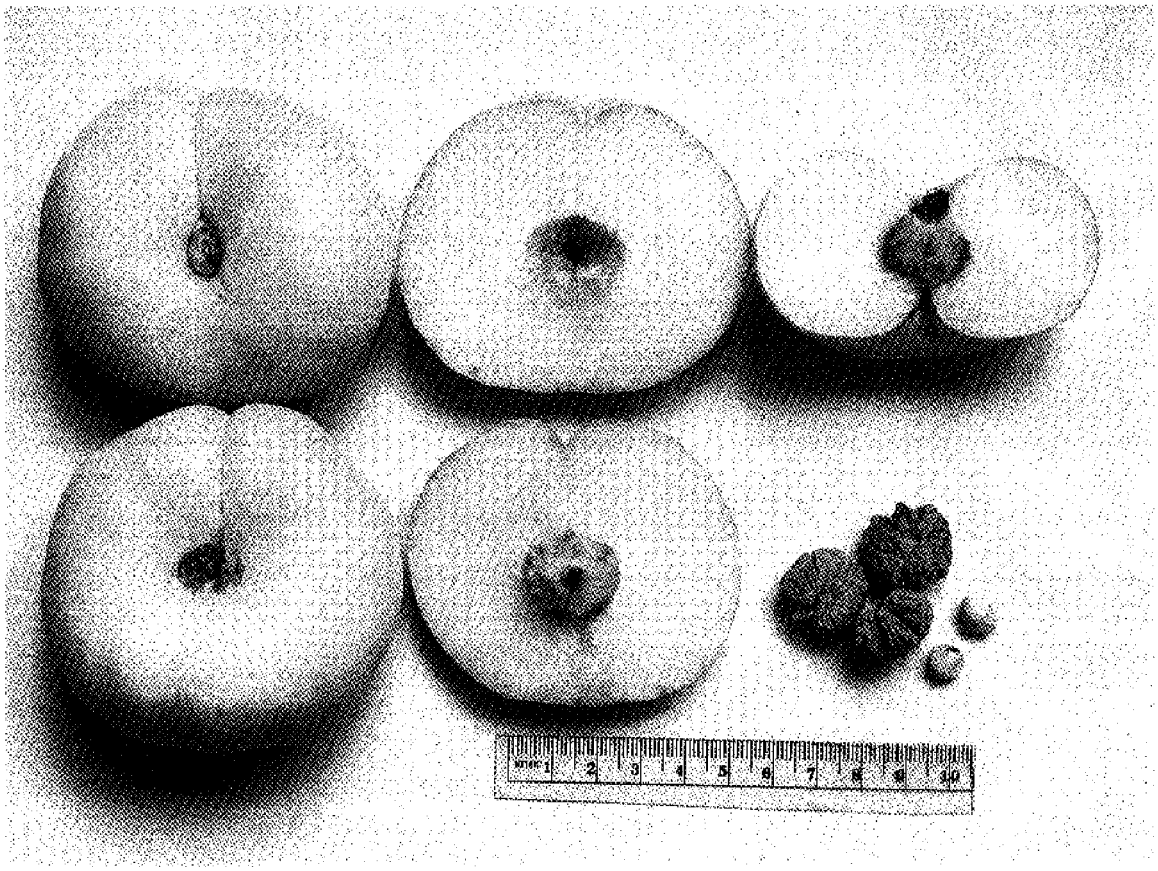
FIG. 2 is a color photograph of mature fruit of 'NJF17' and stones harvested from the Rutgers Fruit Research and Extension Center in Cream Ridge, N.J. on Aug. 16, 2005. Whole fruit are presented in two positions, a basal view (upper left) and an apical view (lower left). Transverse cross sections (upper center and lower center) show that the pericarp clings to the pit when the fruit is mature. A longitudinal cross section (upper right) shows the oblate form of the fruit. The stones (lower right) illustrate the high and deeply grooved ventral suture and the mixture of pits and chains of pits forming grooves on the surface of the stone.
Figure 3:
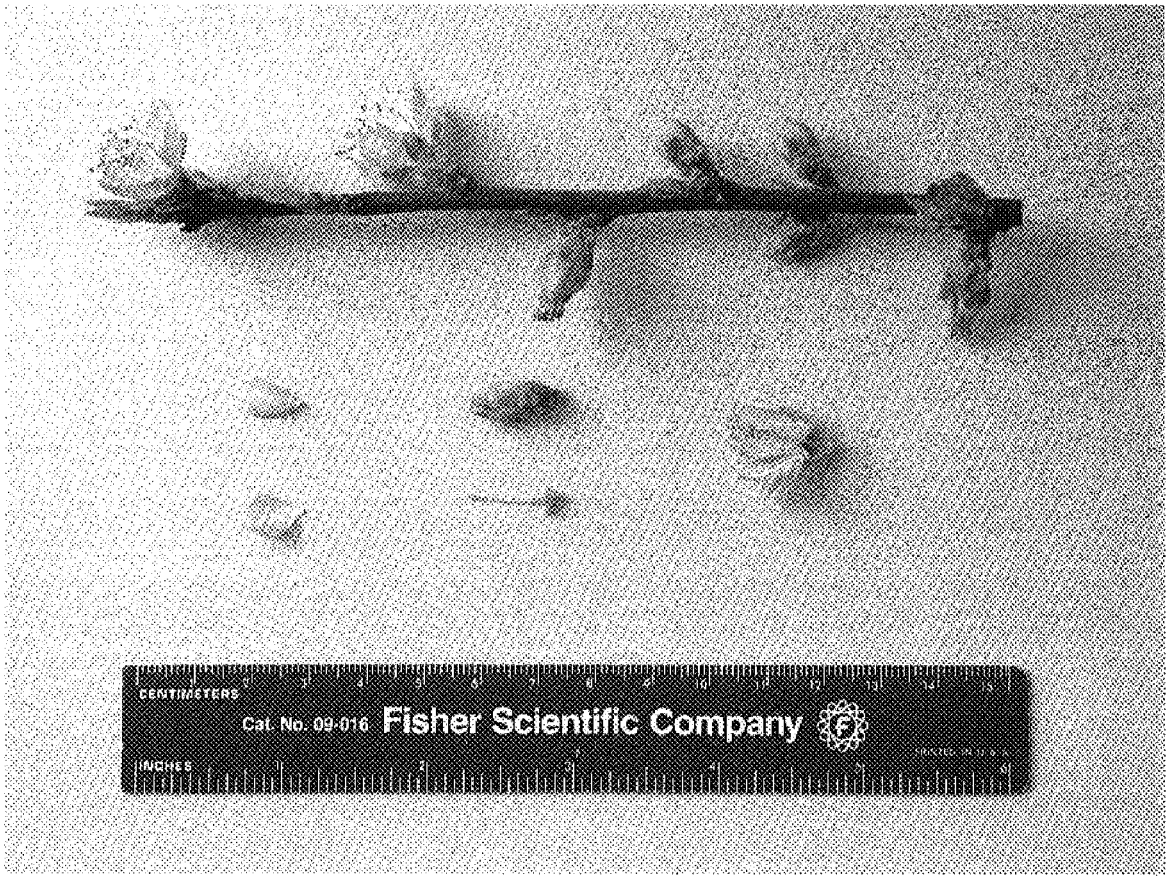
FIG. 3 is a color photograph of a characteristic twig that illustrates the typical flower buds and non-showy flowers of 'NJF17' observed on a tree at the Rutgers Fruit Research and Extension Center in Cream Ridge, N.J. on Apr. 16, 2005.
Figure 4:
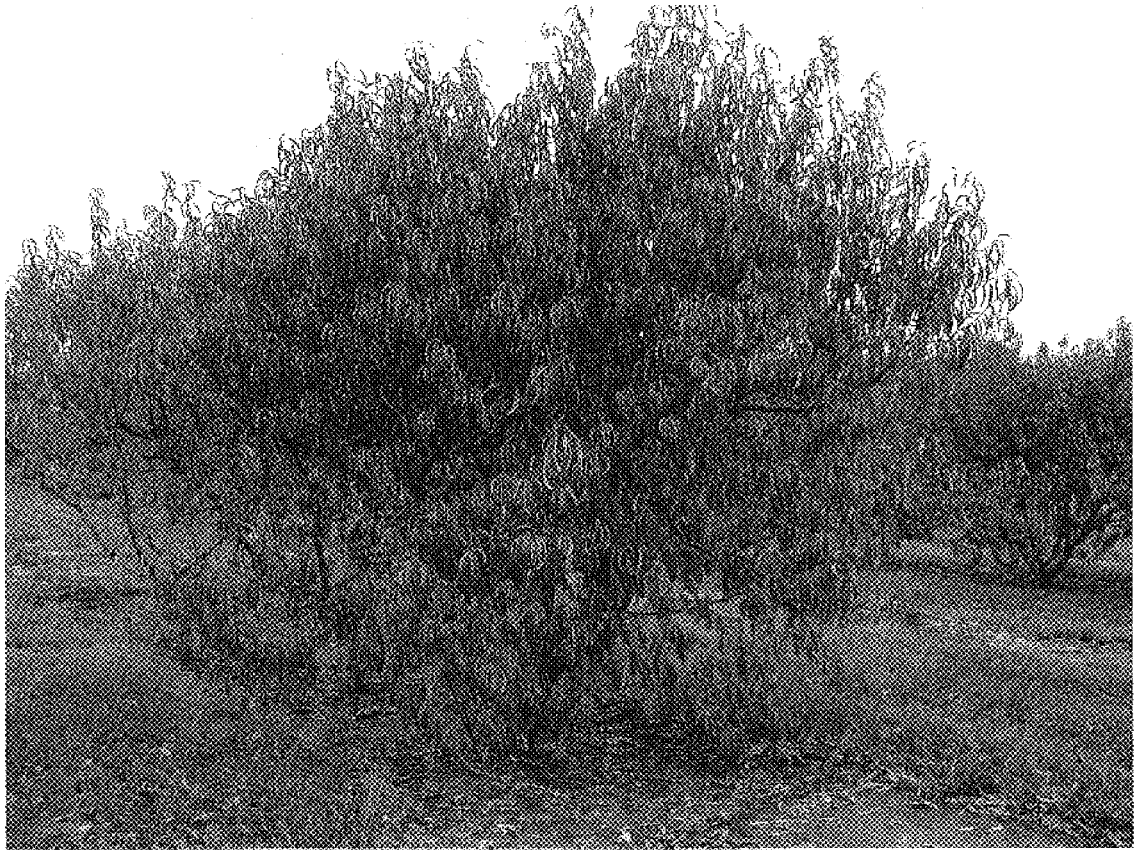
FIG. 4 is a color photograph of a tree of 'NJF17' in early fall that illustrates the slightly upright growth habit of a tree at the Rutgers Fruit Research and Extension Center in Cream Ridge, N.J. on Oct. 27, 2005.
Figure 5:
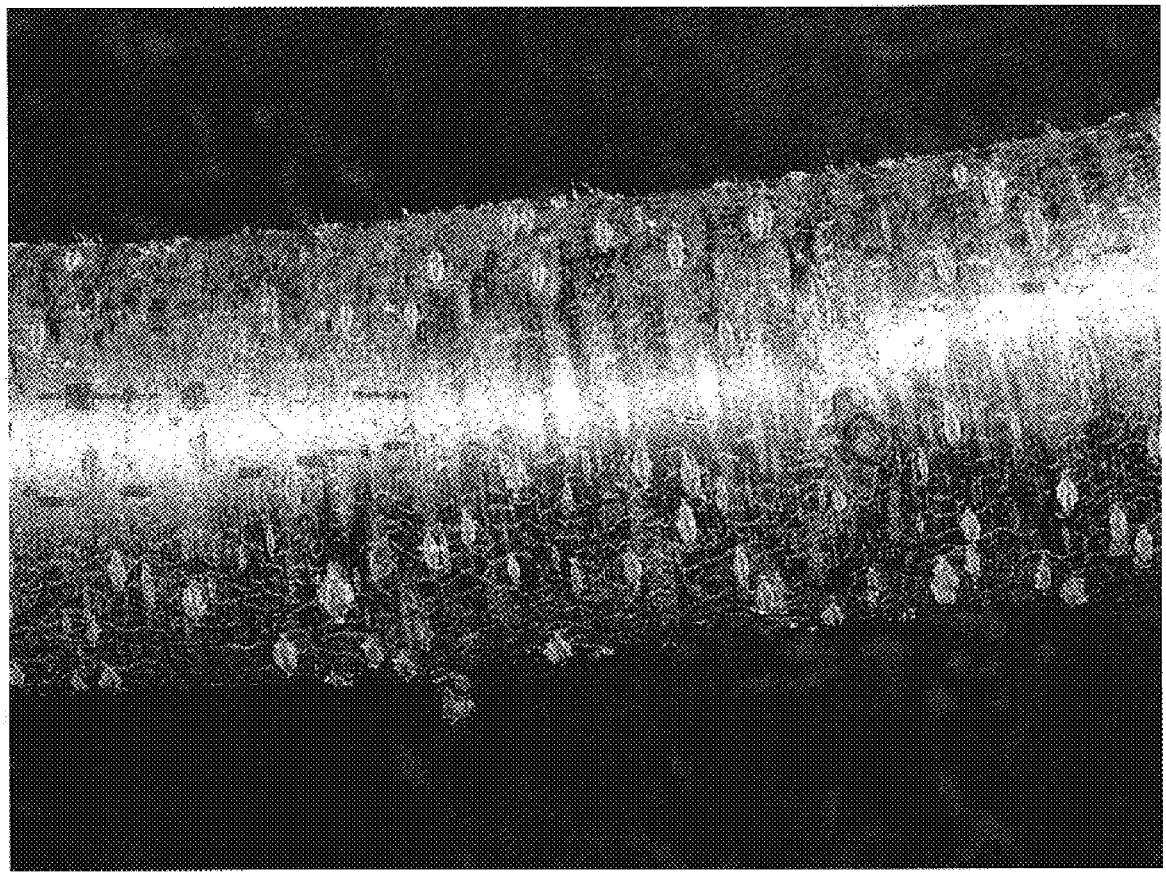
FIG. 5 is a color photograph taken on Oct. 27, 2005 of immature bark of 'NJF17' that illustrates color and the moderate density of elliptical lenticels on the immature bark.
Figure 6:
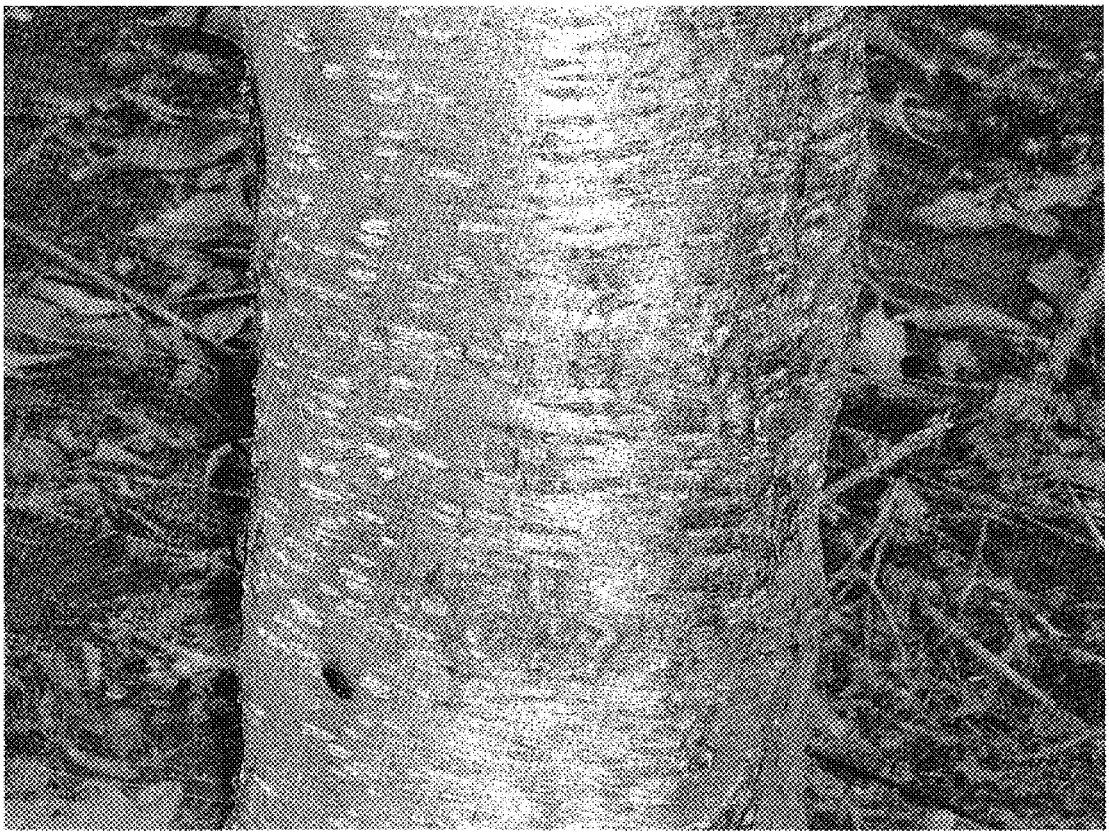
FIG. 6 is a color photograph taken on Oct. 27, 2005 of mature bark of 'NJF17' that illustrates the slightly rough texture of the mature bark.

The following detailed description of the 'NJF17' variety is based on observations of an asexually reproduced tree. The observed tree was 7 years of age and growing on 'Lovell' seedling rootstock (unpatented) in Research Block C at the Rutgers Fruit Research and Extension Center in Cream Ridge, N.J.

Scientific name: *Prunus persica* L.
Parentage:

| | |
|---|---|
| Seed parent: | A43-143-782081. |
| Pollen parent: | D33-1-86227. |

Tree:

| | |
|---|---|
| Vigor: | Vigorous. |
| Plant hardiness zone: | Growth of plants has only been observed in zone 6b. |
| Dormant flower bud cold tolerance: | At least to −13° C. |
| Overall shape: | Slightly upright with a well rounded canopy. |
| Height: | Above average as compared to other peach cultivars. For example, measurement of a typical grafted tree on 'Lovell' seedling rootstock (unpatented) at 7 years after planting shows an average height of 4.3 meters when grown in Cream Ridge, New Jersey. |
| Width: | Below average as compared to other peach cultivars. For example, measurement of a typical grafted tree on 'Lovell' seedling rootstock (unpatented) at 7 years after planting shows an average width of 4.1 meters when grown in Cream Ridge, New Jersey. |
| Caliper: | Seven year old tree is 48 cm in circumference measured at 20 cm from the ground. |
| Trunk and Branches: | |
| Trunk bark texture: | Slightly rough. |
| Trunk bark color: | Under color is greyed-red (RHS 156b) overlaid by greyed-orange (RHS 174d) vertical cracks. |
| Primary branches: | Branches that are approximately 15 cm in circumference are greyed orange (RHS 177a) in color, overlaid with greyed-white (RHS 156b). |
| Lenticels: | Moderate density, approximately 2 to 3 per square cm; elliptical shape, typical examples of which measured 5.5 mm in length; greyed-orange (RHS 165b) in color, bordered with greyed-white (RHS 156d). |
| Branch pubescence: | None. |
| New growth bark: | Color is greyed-orange (RHS 173a) in sun and yellow-green (between RHS 146c to RHS 146d) in shade. |
| Internodes: | Length typically 23 mm to 28 mm, averaging 26 mm on a one-year shoot. |

Leaves:

| | |
|---|---|
| Texture: | Glabrous. |
| Sheen: | Young leaves semi-glossy with a flat finish on the underside. |
| Length: | About 160 mm to 196 mm averaging about 180 mm including the petiole. |
| Width: | About 30 mm to 39 mm averaging about 35 mm. |
| Petiole: | About 11.2 mm long and about 1.4 mm in diameter. |
| Margin: | Serrulate. |
| Margin undulation: | Slightly wavy and crinkled. |
| Form: | Lanceolate. |
| Apex: | Acuminate, curved downward. |
| Base: | Broadly acute. |
| Venation: | Pinnate. |
| Glands: | |
| Number: | About 0 to 5, averaging about 3. |
| Position: | Located on petiole and leaf margin. |
| Size: | Length averaging 1.0 mm and width averaging 0.9 mm. |
| Form: | Reniform. |
| Stipules: | None observed on mature leaves. |
| Leaf Color: | |
| Upper leaf surface: | Green (RHS 137a). |
| Lower leaf surface: | Yellow-green (RHS 147b). |
| Vein: | Yellow-green (RHS 147c). |
| Pubescence: | None. |

Flowers:

| | |
|---|---|
| Size: | Small size, non-showy, typical flower measuring about 23 mm across. |
| Color: | |
| Dormant bud: | Brown (between RHS 200a and RHS 200b). |
| Pink stage bud: | Red (between RHS 55c and RHS 55d). |
| Open flower: | Open flowers red (RHS 56c) bordered with red (RHS 55b). |
| Petals: | Typically 5 petals per flower; obovate shape; averaging 11.4 mm long and 8.4 mm wide. Color red (RHS 56c), bordered with red (RHS 55b). |
| Petal apex: | Rounded. |
| Petal base: | Acuminate. |
| Stamens: | |
| Number: | Variable, between 37 to 43, averaging about 40.6. |
| Length: | Variable, between 10.0 mm to 13.1 mm, averaging 11.6 mm. |
| Filament color: | Green-white (RHS 157d). |
| Anther color: | Red (RHS 42b). |
| Pistil: | |
| Number: | One. |
| Size: | Length between 10.1 and 14.0 mm, averaging about 12.8 mm. |
| Pistil color: | Yellow-green (RHS 144b). |
| Ovary: | Moderately pubescent, and oblate in shape. |
| Sepals: | |
| Number: | Five. |

-continued

| | |
|---|---|
| Color: | Ground color yellow green (RHS 144c), overlaid with greyed-red (RHS 182d) and light pubescence. |
| Shape: | Triangular, with a rounded apex. |
| Size: | Length averaging about 5.0 mm, width averaging about 4.0 mm. |
| Nectar cup color: | Greyed-yellow (RHS 162 b). |
| Pollen: | Abundant. |
| Fragrance: | Very slight. |
| Bloom season: | Onset of bloom in 2005 on April 17; full bloom on April 20. |

Fruit:

| | |
|---|---|
| Size: | Medium, about 4.1 cm long, 7.6 cm wide perpendicular to the suture and 6.9 cm wide parallel to the suture. |
| Typical weight: | 131 g. |
| Form: | |
| Longitudinal section: | Oblate. |
| Traverse section: | Round-oblate. |
| Suture: | Moderately depressed. |
| Base: | Truncated and indented. |
| Apex: | Depressed; between nearly 13 to about 25 mm in diameter, with an average of 17.7 mm. |
| Stem: | Average length of 5.3 mm and an average diameter of 9.7 mm. |
| Skin: | |
| Thickness: | Average. |
| Surface: | Regular with short pubescence. |
| Tenacity: | Above average. |
| Astringency: | Generally none. |
| Tendency to crack: | High in some years. |
| Color: | Under color green-yellow (RHS 1c) when firm ripe, becoming yellow (between RHS 4c and RHS 10c) when fully ripe. Typically there is no over color. |
| Fruit Properties: | |
| Flesh color: | Yellow (RHS 10c). |
| Flesh adhesion: | Clingstone. |
| Juice: | Moderate. |
| Texture: | Fine, nonmelting. |
| Fibers: | Not noticeable. |
| Ripens: | Between July 27 and August 14 at Cream Ridge, New Jersey. |
| Flavor: | Develops a sweet and spicy flavor when fully mature. |
| Soluble solids: | 14.8%. |
| Aroma: | Moderate. |
| Eating quality: | Excellent. |
| Keeping quality: | Good. Has held its flavor and firmness for at least 21 days in cold storage at 1° to 4° C. |

-continued

| | |
|---|---|
| Shipping quality: | Fair. Although no bruising or scaring disorders have been observed, lack of red over color makes blemishes more visible. |
| Usage: | Desert. |
| Market: | Local and long distance. |
| Productivity: | Good for a flat peach. Tree has produced a crop in 6 out of 6 years, and a full crop in 3 out of 6 years. |

Stone:

| | |
|---|---|
| Type: | Clingstone. |
| Form: | Oblate. |
| Base: | Very broad. |
| Apex: | Very broad. |
| Surface: | Mixture of pits and chains of pits forming grooves. |
| Ventral suture: | High, medium width, and deeply grooved on both sides. |
| Dorsal ridge: | Low, narrow width, and deep lines. |
| External color: | Greyed-orange (between RHS 165d and RHS 166a). |
| Internal color when cracked: | Greyed-orange (RHS 165d). |
| Cavity surface color: | Greyed-orange (RHS 165c). |
| Average stone weight: | Dry weight 2.7 g. |
| Average stone wall thickness: | Variable, averaging about 4.2 mm. |
| Size: | Very small. Averages about 13.2 mm long, 19.5 mm wide parallel to the dorsal ridge and 19.6 mm wide perpendicular to the dorsal ridge. |
| Tendency to split: | Moderate in some years, especially when inadequately cropped. |
| Kernel: | |
| Form: | Irregular. |
| Skin color: | Orange-white (between RHS 159 b and RHS 159c) at harvest, becoming greyed-orange (RHS 165b) when dried. |
| Vein color: | Greyed-orange (RHS 165c) at harvest, becoming greyed-orange (RHS 165b) when dried. |
| Viable: | No. |
| Size: | Highly variable; forms only rudimentary seed. |
| Amygdalin | Present |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *